(12) United States Patent
Takahashi

(10) Patent No.: US 11,737,710 B2
(45) Date of Patent: Aug. 29, 2023

(54) PIEZOELECTRIC SENSOR AND METHOD FOR MANUFACTURING THE SAME

(71) Applicant: Sumitomo Riko Company Limited, Aichi (JP)

(72) Inventor: Wataru Takahashi, Aichi (JP)

(73) Assignee: Sumitomo Riko Company Limited, Aichi (JP)

( * ) Notice: Subject to any disclaimer, the term of this patent is extended or adjusted under 35 U.S.C. 154(b) by 564 days.

(21) Appl. No.: 16/708,462

(22) Filed: Dec. 10, 2019

(65) Prior Publication Data

US 2020/0245947 A1    Aug. 6, 2020

Related U.S. Application Data

(63) Continuation of application No. PCT/JP2019/012105, filed on Mar. 22, 2019.

(30) Foreign Application Priority Data

Jan. 31, 2019 (JP) .................................. 2019-015731

(51) Int. Cl.
  *A61B 5/00* (2006.01)
  *A47C 21/00* (2006.01)
  (Continued)

(52) U.S. Cl.
  CPC ............ *A61B 5/6892* (2013.01); *A47C 21/00* (2013.01); *H10N 30/06* (2023.02); *H10N 30/092* (2023.02);
  (Continued)

(58) Field of Classification Search
  CPC ............. H01L 41/0478; H01L 41/1132; H01L 41/183; H01L 41/29; H01L 41/37
  See application file for complete search history.

(56) References Cited

U.S. PATENT DOCUMENTS

| 5,951,908 A | 9/1999 | Cui et al. |
| 2014/0004364 A1 | 1/2014 | Takahashi et al. |

(Continued)

FOREIGN PATENT DOCUMENTS

| JP | H07204166 | 8/1995 |
| JP | 2001157471 | 6/2001 |

(Continued)

OTHER PUBLICATIONS

Omnexus Silicone Rubber: Complete Guide on Highly Durable Elastomer https://omnexus.specialchem.com/selection-guide/silicone-rubber-elastomer (Year: 2023).*

(Continued)

*Primary Examiner* — Matthew L Reames
(74) *Attorney, Agent, or Firm* — JCIPRNET

(57) ABSTRACT

A piezoelectric sensor (10) having an elongated-sheet shape includes a piezoelectric layer (11) containing an elastomer and piezoelectric particles and electrode layers (12a and 12b) which are disposed with the piezoelectric layer (11) sandwiched between the electrode layers. In the piezoelectric sensor (10), a pressure sensing region (S) has a length of 500 mm or longer in a longitudinal direction thereof; the electrode layers (12a and 12b) contain an elastomer and flaky conductive materials and are capable of elongating by 10% or more in one direction of plane directions; and when a space between one end portion (A) and the other end portion (B) of the pressure sensing region (S) in the longitudinal direction is set as a measurement zone, an electrical resistance in the measurement zone in the electrode layers (12a and 12b) is 3,000Ω or lower, and the specific Expression (I) is satisfied.

4 Claims, 2 Drawing Sheets

(51) Int. Cl.
  *H10N 30/06* (2023.01)
  *H10N 30/092* (2023.01)
  *H10N 30/30* (2023.01)
  *H10N 30/85* (2023.01)
  *H10N 30/87* (2023.01)
  *H10N 30/88* (2023.01)
  *A61B 5/11* (2006.01)
  *A61B 5/113* (2006.01)

(52) U.S. Cl.
  CPC ......... *H10N 30/302* (2023.02); *H10N 30/852* (2023.02); *H10N 30/878* (2023.02); *H10N 30/883* (2023.02); *A61B 5/1102* (2013.01); *A61B 5/113* (2013.01)

(56) References Cited

U.S. PATENT DOCUMENTS

| | | | |
|---|---|---|---|
| 2014/0210309 A1* | 7/2014 | Miyoshi | G10H 3/143 310/313 A |
| 2018/0233250 A1 | 8/2018 | Taguchi et al. | |

FOREIGN PATENT DOCUMENTS

| | | |
|---|---|---|
| JP | 2014124310 | 7/2014 |
| JP | 2015210927 | 11/2015 |
| JP | 2018056287 | 4/2018 |
| WO | 2017010135 | 1/2017 |
| WO | 2017169627 | 10/2017 |

OTHER PUBLICATIONS

Aurelio L. Araujo, et al., "A Viscoelastic Sandwich Finite Element Model for the Analysis of Passive, Active and Hybrid Structures." Applied Composite Materials, vol. 17, No. 5, Apr. 15, 2020, pp. 529-542.
"Search Report of Europe Counterpart Application", dated Sep. 23, 2020, p. 1-p. 8.
"Office Action of China Counterpart Application", dated Mar. 16, 2023, with English translation thereof, p. 1-p. 17.

* cited by examiner

PIEZOELECTRIC SENSOR AND METHOD FOR MANUFACTURING THE SAME

CROSS-REFERENCE TO RELATED APPLICATIONS

This application is a continuation application of International Application number PCT/JP2019/012105, filed on Mar. 22, 2019, which claims the priority benefit of Japan Patent Application No. 2019-015731, filed on Jan. 31, 2019. The entirety of each of the above-mentioned patent applications is hereby incorporated by reference herein and made a part of this specification.

BACKGROUND

Technical Field

The present disclosure relates to a piezoelectric sensor being elongated and flexible and including a piezoelectric layer and an electrode layer which contain an elastomer.

Related Art

A piezoelectric material that can convert mechanical energy into electrical energy is widely used in pressure sensors, acceleration sensors, vibration sensors, impact sensors, or the like. The piezoelectric material may be ceramics such as lead zirconate titanate (PZT), a polymer such as polyvinylidene fluoride (PVDF) or polylactic acid, a complex obtained by filling a polymer matrix with piezoelectric particles, or the like.

In recent years, with a purpose of healthcare or detection and medical treatment of diseases, or in order to estimate a health condition of a driver in a driver monitoring system, a technology in which a piezoelectric sensor using a piezoelectric material is used to measure biological information such as a respiratory condition or a heart rate has been developed.

For example, as a device that measures biological information of a sleeping subject, a biological information measuring panel including bottom boards made of silicone rubber and a piezoelectric film sensor that detects strain of the bottom board which is produced due to biological activity of the subject is disclosed in Patent Literature 1.

LITERATURE OF RELATED ART

Patent Literature

Patent Literature 1: Japanese Patent Laid-Open No. 2014-124310
Patent Literature 2: International Publication No. WO2017/010135
Patent Literature 3: Japanese Patent Laid-Open No. 2018-56287
Patent Literature 4: Japanese Patent Laid-Open No. 2015-210927
Patent Literature 5: International Publication No. WO2017/169627

As disclosed in Patent Literature 1, in order to measure biological information of the sleeping subject, a measurement device is disposed to extend in a shoulder-width direction of the subject. In this case, when the measurement device is inflexible, the subject feels discomfort such as hardness or stiffness when the subject lies on the measurement device. Additionally, the subject is conscious of a piezoelectric sensor, and thus there is a concern that it is not possible to accurately measure a heart rate or sleep is disturbed.

In this respect, the biological information measuring panel disclosed in Patent Literature 1 employs the bottom boards made of silicone rubber. Besides, the piezoelectric sensor is disposed between two bottom boards so as not to overlap the subject, and the piezoelectric sensor detects strain of the bottom boards which is produced due to biological activity of the subject. Here, an installation location of the piezoelectric sensor is not below the subject. That is, vibration produced due to the biological activity of the subject reaches the piezoelectric sensor through the bottom board. However, the bottom board made of silicone rubber has viscoelasticity, and thus the vibration produced due to the biological activity of the subject is significantly attenuated during a period in which the vibration is transmitted to the piezoelectric sensor. Therefore, it is difficult to detect weak vibration of respiration and heartbeats with high accuracy.

Even when the subject moves by turning over while sleeping, in order to accurately detect biological information thereof, it is desirable to use an elongated piezoelectric sensor so that the piezoelectric sensor overlaps the subject. In this case, an electrode layer is also formed into an elongated shape. A terminal, to which wiring or the like is connected, is usually disposed at one end portion of the electrode layer. Here, when the electrode layer has an elongated shape, a problem arises in that an electrical resistance increases and conductivity decreases in a direction separated (far apart) from the terminal. When the electrical resistance of the electrode layer is high (conductivity is low), electromotive voltage generated in the piezoelectric layer is lowered in the electrode layer, and an output voltage is low. In other words, sensitivity of the piezoelectric sensor is reduced. In view of the problem, a countermeasure for increasing an amount of a conductive material in the electrode layer is considered. However, when the amount of the conductive material increases, the electrode layer hardens (Young's modulus increases), and flexibility of the electrode layer and the piezoelectric sensor is inhibited.

Patent Literatures 2 and 3 disclose a flexible piezoelectric sensor including a piezoelectric layer and an electrode layer which contain an elastomer. Patent Literatures 2 and 3 describe volume resistivity of the electrode layer from the viewpoint of maintaining conductivity even during elongation; however, there is no sprit for forming a piezoelectric sensor into an elongated shape. Therefore, Patent Literatures 2 and 3 do not provide a study on the problem of a decrease in conductivity which occurs when the electrode layer is formed into an elongated shape and do not provide a suggestion for solving the problem either.

Patent Literature 4 discloses, as a conductive film used as an electrode layer of a transducer or the like, a conductive film that contains an elastomer and a conductive material and has a smooth surface with arithmetic average roughness (Ra) of less than 0.5 μm. Patent Literature 4 discloses that the conductive film is formed to have a smooth surface, and thereby it is possible to improve adhesiveness to a counterpart member so as to suppress peeling; however, there is no sprit for forming the electrode layer into an elongated shape. Patent Literature 5 discloses, as a conductive film used as an electrode layer of a transducer or the like, a conductive film that contains an elastomer and flaky carbon materials and has surface glossiness of higher than 0.4% and lower than 10%. Patent Literature 5 discloses that the flaky carbon materials are oriented along a surface of the conductive film, and thereby it is possible to increase conductivity and maintain high conductivity even during elongation; however, there is no sprit for forming the electrode layer into an elongated shape.

The present disclosure is made with consideration for such a circumstance, and an object thereof is to provide a flexible piezoelectric sensor that has a small decrease in conductivity in an electrode layer even when the piezoelectric sensor is elongated and thus has a good sensitivity.

SUMMARY (1) In order to achieve the object described above, a piezoelectric sensor of the present disclosure has an elongated-sheet shape, the piezoelectric sensor including a piezoelectric layer containing an elastomer and piezoelectric particles and electrode layers which are disposed with the piezoelectric layer sandwiched between the electrode layers; when a region in which the electrode layers overlap each other via the piezoelectric layer is set as a pressure sensing region, the pressure sensing region has a length of 500 mm or longer in a longitudinal direction thereof; the electrode layers contain an elastomer and flaky conductive materials and are capable of elongating by 10% or more in one direction of plane directions, and when a space between one end portion and the other end portion of the pressure sensing region in the longitudinal direction is set as a measurement zone, an electrical resistance in the measurement zone in the electrode layers is 3,000Ω or lower; when the electrode layers disposed with one piezoelectric layer sandwiched therebetween are set as a first electrode layer and a second electrode layer, the following Expression (I) is satisfied.

(Young's Modulus of Piezoelectric Layer×Thickness of Piezoelectric Layer)≥{(Young's Modulus of First Electrode Layer×Thickness of First Electrode Layer)+(Young's Modulus of Second Electrode Layer×Thickness of Second Electrode Layer)}     (I)

(2) A method of manufacturing the piezoelectric sensor of the present disclosure includes a coating-film forming step in which a conductive coating material for forming the electrode layers is coated on a surface of a base member by a die-coating method or a dispenser method to form an electrode-layer forming coating film and a press-attaching step in which the electrode-layer forming coating film and the piezoelectric layer are overlapped and press-attached before cross-linking of the formed electrode-layer forming coating film is completed.

Figure 1:
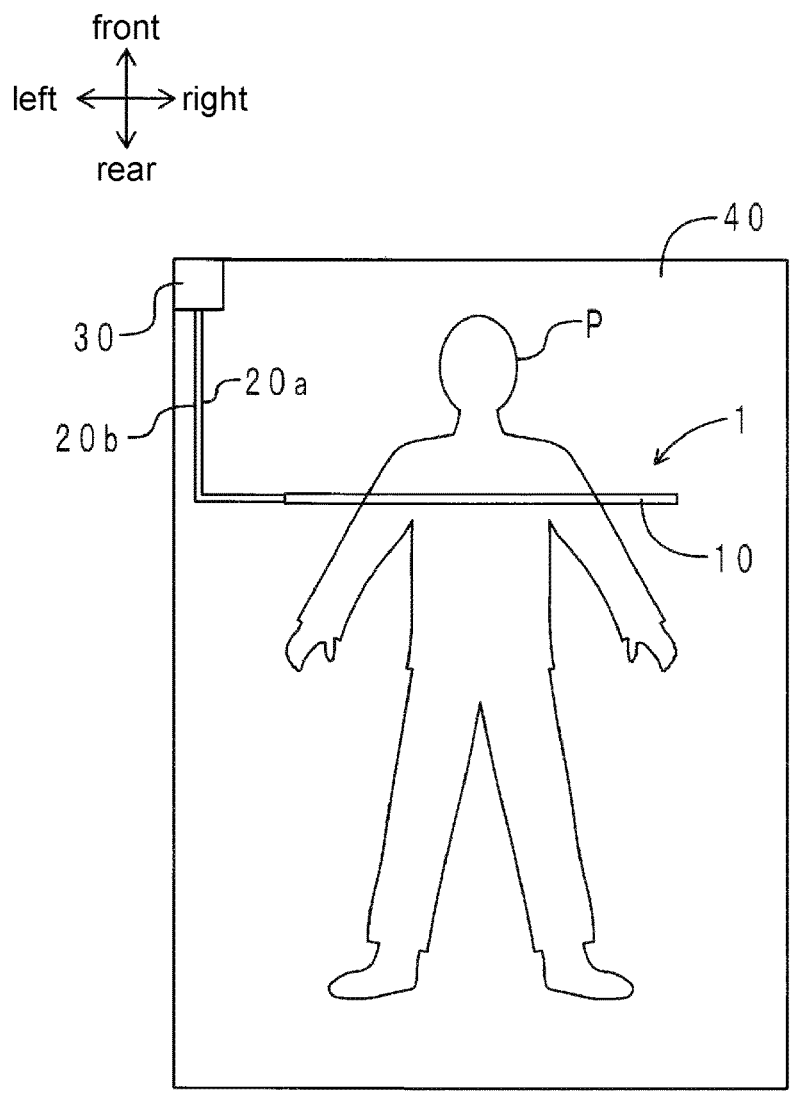
FIG. 1 is a view of disposition of a piezoelectric sensor being an embodiment of the present disclosure.

DESCRIPTION OF THE EMBODIMENTS (1) The piezoelectric sensor of the present disclosure is a sensor having an elongated-sheet shape and includes a pressure sensing region having a length of 500 mm or longer. Therefore, when the piezoelectric sensor of the present disclosure is disposed on bedding to measure biological information of a subject, the pressure sensing region easily overlaps a part of the subject's body. Thus, it is possible to detect without missing weak vibration due to respiration and heartbeats. In the present disclosure, when a length of the piezoelectric sensor is 500 mm or longer, the piezoelectric sensor is described to have an "elongated" shape.

When the pressure sensing region has a length of 500 mm or longer, the electrode layers have the same length as the length of the pressure sensing region. Conventionally, when the piezoelectric sensor has an elongated shape as described above, conductivity decreases in a direction separated from one end portion of the electrode layer at which a terminal is disposed, and it is not possible to realize a desired sensor sensitivity at the entire pressure sensing region. In this respect, the electrode layers that configure the piezoelectric sensor of the present disclosure contain an elastomer and flaky conductive materials. The flaky conductive materials have a relatively high aspect ratio (length/thickness). Therefore, even when a blending amount of the flaky conductive materials does not increase too much, the flaky conductive materials easily come into contact with each other, and a conduction path is easily formed. Therefore, while flexibility is secured, an electrical resistance is unlikely to increase even when the length of the electrode layers increases, and high conductivity can be maintained. Specifically, the electrical resistance in a measurement region (between the one end portion and the other end portion in a longitudinal direction) in the electrode layers is 3,000Ω or lower. Additionally, when the flaky conductive materials are oriented in a manner that a length direction thereof is coincident with a plane direction of the electrode layer, the conductivity can be further increased, and the conduction path is unlikely to be cut even during elongation. As described above, the piezoelectric sensor of the present disclosure includes the electrode layer having high conductivity from one end portion to the other end portion and thus has high sensitivity even in an elongated shape.

The electrode layer is capable of elongating by 10% or more in one direction of the plane directions and has good flexibility in that the previous Expression (I) is satisfied. Since the electrode layer is flexible, the electrode layer can be deformed following deformation such as bending, and a load can be accurately transmitted to a piezoelectric layer. This is also effective in improving sensitivity of the piezoelectric sensor. In addition, satisfaction of (I) means that a ratio of an external force applied to the piezoelectric layer with respect to an external force applied to the piezoelectric sensor increases. In this case, in accordance with the following Expression (II), a quantity of electric charge generated in the piezoelectric layer increases. The quantity of generated electric charge is proportional to sensor output. In other words, when Expression (I) is satisfied, the sensor output increases. Quantity of Generated Electric Charge (C) in Piezoelectric Layer=Sensor Sensitivity (C/N)×External Force Applied to Piezoelectric Layer     (II)

In addition, even when the piezoelectric sensor of the present disclosure is disposed on bedding and the subject lies on the bedding, the subject is unlikely to feel a discomfort such as hardness or stiffness. Additionally, the piezoelectric sensor is capable of extending and contracting following movement of the subject or the bedding. Therefore, it is possible to precisely detect weak vibration due to respiration and heartbeats or a respiratory sound derived from the respiration and the heartbeats.

(2) In a method for manufacturing the piezoelectric sensor of the present disclosure, first, a die-coating method or a dispenser method is used to form an electrode-layer forming coating film. A conductive coating material for forming the electrode layer contains flaky conductive materials. The flaky conductive materials are dispersed in a liquid conductive coating material in random directions. When the conductive coating material is coated on a base member, if the die-coating method and the dispenser method are used, a shear force is applied to the conductive coating material. The flaky conductive materials contained in the conductive coating material are oriented by the shear force in a manner that the length direction of the flaky conductive material is coincident with a forming direction of the coating film, that is, the length direction of the flaky conductive materials is horizontal with respect to a surface of the coating film. Consequently, a conduction path is easily formed in the longitudinal direction of the electrode layer. As a result, the electrical resistance is unlikely to increase even when the length of the electrode layers increases, and high conductivity can be realized. In addition, when the flaky conductive materials are oriented, unevenness on the surface of the coating film decreases, an adhering area with the piezoelectric layer increases and adhesiveness can be increased. When the unevenness on the surface of the electrode layer decreases, a gap between the piezoelectric layer and the electrode layer decreases, and thus the sensitivity of the piezoelectric sensor effectively improves.

Subsequently, in the method for manufacturing the piezoelectric sensor of the present disclosure, the coating film and the piezoelectric layer are overlapped and press-attached to each other before cross-linking of the formed electrode-layer forming coating film is completed. Consequently, the surface of the coating film is further smoothened, the adhering area with the piezoelectric layer increases and the adhesiveness can be further increased. When the adhesiveness is high, the piezoelectric layer and the electrode layers are unlikely to peel off even when extending and contracting are repeated, and thus durability of the sensor improves. As described above, according to the manufacturing method of the present disclosure, the adhering area of the electrode layers with the piezoelectric layer increases and the adhesiveness can be improved. Hence, an elongated piezoelectric sensor having high sensitivity can be manufactured.

As an embodiment of a piezoelectric sensor of the present disclosure, an example of using a piezoelectric sensor as a biological information detecting device is described.

Figure 2:
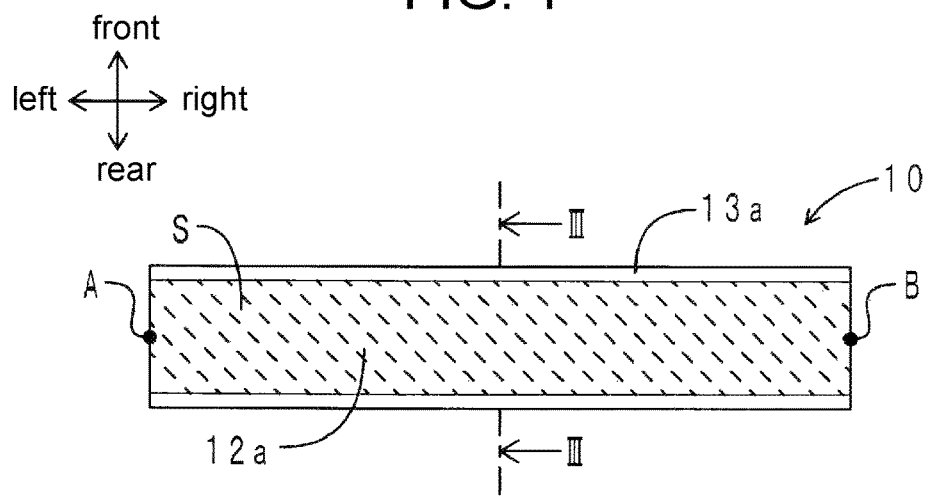
FIG. 2 is a top view of the piezoelectric sensor.
Figure 3:
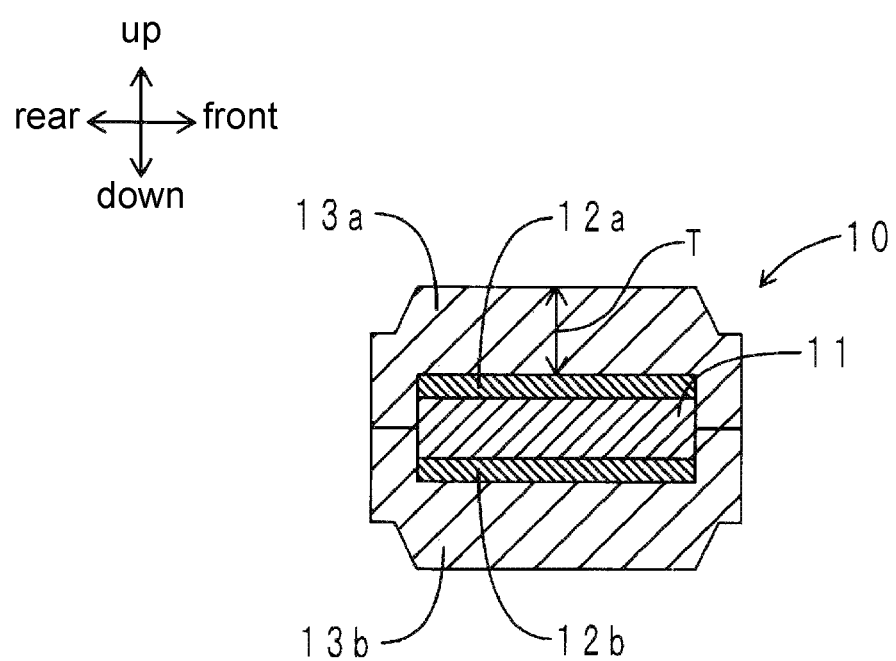
FIG. 3 is a sectional view taken along line III-III in FIG. 2.

FIG. 1 is a view of disposition of the biological information detecting device of the embodiment. FIG. 2 is a top view of the piezoelectric sensor in the biological information detecting device. FIG. 3 is a sectional view taken along line III-III in FIG. 2. FIG. 1 is a view through the biological information detecting device.

As shown in FIGS. 1 to 3, a biological information detecting device 1 includes a piezoelectric sensor 10, wiring 20a and 20b, and a control circuit unit 30. In the embodiment, in a state in which a subject P sleeps on the back on a mattress, a shoulder-width direction of the subject P is defined as a right-left direction, and a height direction thereof is defined as a front-rear direction. A width of the piezoelectric sensor 10 is a length in the front-rear direction, and a length thereof is a length in the right-left direction. The piezoelectric sensor 10 is fixed to a back side of a cover 40 that covers the mattress of a bed.

The piezoelectric sensor 10 is disposed to extend in a strip-like shape in the right-left direction. A part of the piezoelectric sensor 10 is disposed below the chest of the subject P. The piezoelectric sensor 10 has a rectangular-sheet shape having a width of 50 mm, a length of 900 mm, and a thickness of 0.575 mm (575 µm). The piezoelectric sensor 10 has an elongated shape and includes a piezoelectric layer 11, a pair of electrode layers 12a and 12b, and a pair of protective layers 13a and 13b.

The piezoelectric layer 11 contains carboxyl group-modified hydrogenated nitrile rubber (XH-NBR) and lithium sodium potassium niobate particles. A content of the lithium sodium potassium niobate particles is 48 volume % when a volume of the XH-NBR is set as 100%. The piezoelectric layer 11 has a rectangular thin-film shape having a width of 40 mm, a length of 900 mm, and a thickness of 0.035 mm (35 µm). The Young's modulus of the piezoelectric layer 11 is 80 MPa. The piezoelectric layer 11 is subjected to a polarization treatment, and the lithium sodium potassium niobate particles are polarized in a thickness direction (up-down direction) of the piezoelectric layer 11.

The electrode layer 12a contains glycidyl ether group-modified acrylic rubber and flaky carbon materials. The electrode layer 12a has a rectangular thin-film shape having a width of 40 mm, a length of 900 mm, and a thickness of 0.02 mm (20 µm). The electrode layer 12a is disposed on a top surface of the piezoelectric layer 11. The wiring 20a is connected to a left end portion of the electrode layer 12a via a terminal. A material, a shape, and a size of the electrode layer 12b are the same as those of the electrode layer 12a. The electrode layer 12b is disposed on an undersurface of the piezoelectric layer 11. The wiring 20b is connected to a left end portion of the electrode layer 12b via a terminal. The electrode layers 12a and 12b are both capable of elongating by 10% or more in the right-left direction. The Young's modulus of both the electrode layer 12a and the electrode layer 12b is 35 MPa. An electrical resistance of a space (measurement region) between the left end portion (point A in FIG. 2) and a right end portion (point B in FIG. 2) in the electrode layers 12a and 12b is 675Ω.

The electrode layers 12a and 12b have the same Young's modulus and thickness. In other words, when the two electrode layers disposed with the piezoelectric layer sandwiched therebetween have the same Young's modulus and thickness, the previous Expression (I) can be expressed as the following Expression (Ia).

$$\text{(Young's Modulus of Piezoelectric Layer} \times \text{Thickness of Piezoelectric Layer)} \{(\text{Young's Modulus of Electrode Layer} \times \text{Thickness of Electrode Layer}) \times 2\} \quad \text{(Ia)}$$

When Expression (Ia) is further transformed, the following Expression (Ib) is obtained. Thus, a determination on whether Expression (I) is satisfied can be made by Expression (Ib).

$$\text{(Young's Modulus of Piezoelectric Layer} \times \text{Thickness of Piezoelectric Layer)}/\{(\text{Young's Modulus of Electrode Layer} \times \text{Thickness of Electrode Layer}) \times 2\} \geq 1 \quad \text{(Ib)}$$

In the embodiment, when values of the Young's moduli and the thicknesses of the piezoelectric layer 11 and the electrode layers 12a and 12b are substituted in Expression (Ib) to be computed, 2.0 is obtained. In other words, the piezoelectric sensor 10 satisfies Expression (I).

The protective layer 13a is made of a thermoplastic elastomer and has a rectangular thin-film shape having a width of 50 mm, a length of 900 mm, and a thickness of 0.25 mm (250 µm). The protective layer 13a is disposed on a top surface of the electrode layer 12a. A material, a shape, and a size of the protective layer 13b are the same as those of the protective layer 13a. The protective layer 13b is disposed on an undersurface of the electrode layer 12b. The Young's modulus of both the protective layer 13a and the protective layer 13b is 20 MPa.

The piezoelectric layer 11, the electrode layers 12a and 12b, and the protective layers 13a and 13b have the same length and are different from each other only in width. As shown by hatching with dotted lines in FIG. 2, when viewed from above, a pressure sensing region S (region in which the electrode layers 12a and 12b overlap the piezoelectric layer 11 in the thickness direction) at a central portion of the piezoelectric sensor 10 in a width direction thereof. The pressure sensing region S has a width of 40 mm and a length of 900 mm in the right-left direction (longitudinal direction).

The electrode layer 12a and the control circuit unit 30 are electrically connected via the wiring 20a. The electrode layer 12b and the control circuit unit 30 are electrically connected via the wiring 20b. When a load is applied to the piezoelectric sensor 10 due to respiration and heartbeats of the subject P, electric charges are generated in the piezoelectric layer 11. The generated electric charges (output signal) are detected as a change in voltage or current by the control circuit unit 30. The respiration and heartbeats of the subject are detected based on the detection of the electric charges.

In the embodiment, a base material of both the piezoelectric layer 11 and the electrode layers 12a and 12b which configure the piezoelectric sensor 10 is an elastomer. In addition, the protective layers 13a and 13b are also made of an elastomer. Because each of the layers is flexible, the entire piezoelectric sensor 10 is flexible. Accordingly, even when the piezoelectric sensor 10 is disposed on a mattress, and the subject P lies on the piezoelectric sensor 10, the subject P is unlikely to feel a discomfort such as hardness or stiffness. In addition, the electrode layers 12a and 12b contain the flaky carbon materials, and the electrical resistance between the left end portion and the right end portion is 675Ω. Even when the length of the electrode layers 12a and 12b increases, the electrical resistance is small. As described above, the piezoelectric sensor 10 includes the electrode layers 12a and 12b having high conductivity over the entire length thereof in the longitudinal direction and thus has high sensitivity even in an elongated shape. Besides, the piezoelectric sensor 10 is capable of extending and contracting following movement of the subject P or the mattress, and thus weak vibration due to the respiration and heartbeats can be precisely detected even when the subject P overlaps an end portion of the pressure sensing region S.

One embodiment of the piezoelectric sensor of the present disclosure is described above. The piezoelectric sensor of the present disclosure is not limited to the embodiment described above and can be implemented in various embodiments in which modifications and alterations which can be performed by those skilled in the art are performed within a range without departing from the gist of the present disclosure.

<Piezoelectric Layer>

The piezoelectric layer contains an elastomer and piezoelectric particles. As the elastomer, at least one selected from crosslinked rubbers and thermoplastic elastomers may be used. Flexible elastomers having relative low Young's modulus include urethane rubber, silicone rubber, nitrile rubber (NBR), hydrogenated nitrile rubber (H-NBR), acrylic rubber, natural rubber, isoprene rubber, ethylene-propylene-diene rubber (EPDM), ethylene-vinyl acetate copolymer, ethylene-vinyl acetate-acrylic ester copolymer, butyl rubber, styrene-butadiene rubber, fluoro-rubber, epichlorohydrin rubber, and the like. In addition, an elastomer modified by introducing a functional group or the like may be used. Modified elastomers are preferably hydrogenated nitrile rubbers having at least one group selected from, for example, a carboxyl group, a hydroxyl group, and an amino group.

The piezoelectric particles are particles of a compound having piezoelectricity. As the compound having piezoelectricity, a ferroelectric substance having a perovskite crystal structure is known, and the compound includes, for example, barium titanate, strontium titanate, potassium niobate, sodium niobate, lithium niobate, potassium sodium niobate, lithium sodium potassium niobate, lead zirconate titanate (PZT), barium strontium titanate (BST), bismuth lanthanum titanate (BLT), strontium bismuth tantalate (SBT), and the like. One or two or more kinds thereof may be used as the piezoelectric particles.

A content of the piezoelectric particles may be determined with consideration of flexibility of the piezoelectric layer and the piezoelectric sensor and piezoelectric performance of the piezoelectric layer. When the content of the piezoelectric particles increases, the piezoelectric performance of the piezoelectric layer improves but the flexibility decreases. Accordingly, in a combination of an elastomer and the piezoelectric particles to be used, it is preferable to adjust the content of the piezoelectric particles so as to realize desired flexibility. For example, the content of the piezoelectric particles may be 30 volume % or more and 50 volume % or less when the elastomer is set as 100 volume %.

The piezoelectric layer is manufactured by hardening a composition under a predetermined condition, the composition being obtained by adding powder of the piezoelectric particles, a cross-linker, or the like in an elastomer polymer. Then, the piezoelectric layer is subjected to a polarization treatment. In other words, a voltage is applied to the piezoelectric layer, and a polarization direction of the piezoelectric particles becomes coincident with a predetermined direction.

As a result of study, the present inventors verified that sensitivity to an applied load increases in the sheet-shaped piezoelectric sensor when a sectional area perpendicular to a tension direction of the piezoelectric layer is small. Thus, a thin piezoelectric layer is preferable. For example, the thickness of the piezoelectric layer is preferably 200 μm or smaller, and more preferably 100 μm or smaller. On the other hand, when the piezoelectric layer is too thin, dielectric breakdown is likely to occur during the polarization treatment. Therefore, the thickness of the piezoelectric layer is preferably 10 μm or larger, and more preferably 20 μm or larger.

<Electrode Layer>

The electrode layer contains an elastomer and the flaky conductive materials. The kind of elastomer, the kind and the content of the flaky conductive materials, and the like may be appropriately determined so that the flexibility and the conductivity of the electrode layer are balanced. In terms of flexibility, the electrode layer is configured to elongate by 10% or more in one direction of plane directions. For example, "elongate by 10% in one direction" means that the length of the electrode layer in the direction is 1.1 times of the length in a no-load state. Besides, when the electrode layers disposed with one piezoelectric layer sandwiched therebetween are set as a first electrode layer and a second electrode layer, the following Expression (I) is satisfied.

$$\text{(Young's Modulus of Piezoelectric Layer} \times \text{Thickness of Piezoelectric Layer)} \{ \text{(Young's Modulus of First Electrode Layer} \times \text{Thickness of First Electrode Layer)} + \text{(Young's Modulus of Second Electrode Layer} \times \text{Thickness of Second Electrode Layer)} \} \quad (1)$$

In this specification, the Young's modulus is calculated from a stress-elongation curve obtained by performing a tensile test prescribed in JIS K 7127: 1999. The tensile test is performed using a test piece type 2 at a tensile speed of 100 mm/min.

In terms of conductivity, when a region in which the electrode layers overlap each other via the piezoelectric layer is set as a pressure sensing region, and a space between one end portion and the other end portion of the pressure sensing region in the longitudinal direction is set as a measurement zone, the electrical resistance in the measurement zone in the electrode layers is 3,000Ω or lower. When the electrical resistance in the measurement region is 2,000Ω or lower and even 1,000Ω or lower, it is preferable because the conductivity further increases.

From the viewpoint of having rubber-like elasticity at normal temperature, preferably, an elastomer having a glass-transition temperature (Tg) equal to or lower than room temperature is used as the elastomer. Crystallinity decreases as the Tg decreases. Therefore, the elastomer is more easily extended and contracted. For example, an elastomer having the Tg of 0° C. or lower, −10° C. or lower, or even −30° C. or lower is more flexible and is preferable.

The elastomer is preferably a crosslinked rubber from a reason that the crosslinked rubber has good resilience when a deformation is repeated. In addition, an elastomer that has a microphase-separated structure having a hard segment and a soft segment and is pseudo-crosslinked like a thermoplastic elastomer may be used. The thermoplastic elastomers include an olefin-based elastomer, a styrene-based elastomer, a polyester-based elastomer, an acrylic-based elastomer, a urethane-based elastomer, or a PVC-based elastomer. Crosslinked rubbers include urethane rubber, acrylic rubber, silicone rubber, butyl rubber, butadiene rubber, ethylene oxide-epichlorohydrin copolymer, nitrile rubber (NBR), hydrogenated nitrile rubber (H-NBR), chloroprene rubber, natural rubber, isoprene rubber, styrene-butadiene rubber, ethylene-propylene-diene copolymer (EPDM), polyester rubber, or fluoro-rubber. In addition, an elastomer that is modified, like epoxidized natural rubber or carboxyl group-modified hydrogenated nitrile rubber, by introducing a functional group or the like may be used. Among the above rubbers, acrylic rubber has low crystallinity and a weak intermolecular force and thus has a lower Tg compared with other kinds of rubber. Thus, acrylic rubber is flexible and elongated easily.

The flaky conductive material may be appropriately selected from flaky metal materials and flaky carbon materials. The flaky metal material include silver, gold, copper, nickel, rhodium, palladium, chromium, titanium, platinum, iron, an alloy thereof, metal oxide consisting of zinc oxide, titanium oxide and the like, metal carbide consisting of titanium carbonate and the like. The flaky carbon material can be manufactured by a carbon material having a graphite structure, such as graphite or expanded graphite. The flaky carbon material is preferably a multilayer graphene which is a stack of a plurality of layers of graphene. The graphene is one layer of graphite and has a structure in which six-membered rings of carbon atoms are connected into a planer shape. The number of stacks of graphene in the multilayer graphene is smaller than that of graphite and is preferable several layers to hundreds of layers.

For example, when the flaky carbon material is used, the content of the flaky carbon material is 20 parts by mass or more and 45 parts by mass or less when the entire electrode layers are set as 100 parts by mass. When the content of the flaky carbon material is less than 20 parts by mass, it is difficult for the flaky carbon materials to come into contact with each other, and sufficient conduction paths cannot be formed. Conversely, when the content of the flaky carbon material is more than 45 parts by mass, the Young's modulus of the electrode layer increases, and the flexibility decreases. When the Young's modulus of the electrode layer increases, the ratio of the external force applied to the piezoelectric layer decreases. Hence, the previous Expression (I) is not satisfied, leading to a decrease in the sensor sensitivity.

The electrode layer may contain additives such as a cross-linker, a cross-linking promoter, a cross-linking aid, a plasticizer, a processing aid, an antioxidant, a softener, a colorant, and the like. The cross-linker, the cross-linking promoter, and the cross-linking aid which contribute to a cross-linking reaction may be appropriately selected depending on the type of the elastomer. When the plasticizer is contained, low-temperature resistance of the electrode layer improves. The plasticizers include adipic acid diester, ether-ester derivative, and the like.

When the flaky carbon materials are used, it is preferable to blend the dispersant in order to suppress clumping of the flaky carbon materials and improve dispersibility. The dispersants include polymer surfactant (for example, high-molecular-weight polyester acid amidoamine salt or the like) having an organic salt structure in which an anion and a cation are ion-bonded to each other, a polymer formed by an amide bond or an imide bond between a polycyclic aromatic component and an oligomer component, and the like.

In a case of the former high-molecular-weight polyester acid amidoamine salt, amine groups are adsorbed onto the flaky carbon materials, and a dispersibility improving effect is exerted. In addition, an influence on the conductivity decreases, and a surface of the electrode layer is easily smoothened.

The polycyclic aromatic component in the latter polymer has a π-π interaction and contributes to an affinity with the flaky carbon material. The polycyclic aromatic component has a multi-ring structure including an aromatic ring. The number and the arrangement of rings are not particularly limited. Preferably, the polycyclic aromatic component has, for example, any one of a benzene ring, a naphthalene ring, an anthracene ring, a phenanthrene ring, a pyrene ring, a perylene ring, and a naphthacene ring. With consideration of the flexibility, a biphenyl structure in which the benzene rings are connected to each other or a structure having the naphthalene rings is preferable. The oligomer component having the amide bond or the imide bond with the polycyclic aromatic component contributes to affinity with the elastomer. The oligomer component compatible with the elastomer is preferable.

The adhesiveness between the piezoelectric layer and the electrode layer influences the sensitivity and the durability of the piezoelectric sensor. The high adhesiveness between the piezoelectric layer and the electrode layer is achieved due to an increase in adhering area between the two layers. When the adhering area increases, electric charges generated in the piezoelectric layer can be output without leaking from the electrode layer. In addition, when the adhesiveness is high, the piezoelectric layer and the electrode layers are unlikely to peel off even when the extending and contracting are repeated, and thus the durability of the sensor improves. From the viewpoint of increasing adhesiveness, a peeling strength of the electrode layer with respect to the piezoelectric layer is preferably 2 N/25 mm or higher.

In this specification, the peeling strength is measured by performing a 90° peeling test in accordance with "10. 4 measurement of peel adhesion" in JIS Z 0237: 2009, and an average value of measured values of peeling forces under a peeling length of 100 mm when the peeling lengths range from 25 mm to 125 mm is adopted. The 90° peeling test is performed in a condition of a tensile width of 25 mm and a tensile speed of 300 mm/min under room temperature.

<Protective Layer>

From the viewpoint of protecting an insulation property of the piezoelectric sensor and suppressing damage caused by mechanical stress from outside, a protective layer may be disposed to be stacked on at least one of the electrode layers. Here, from the viewpoint that the protective layer increases strain of the piezoelectric layer and improves the sensitivity of the sensor without restricting deformation of the piezoelectric layer and the electrode layers, it is preferable that the protective layer contains an elastomer. For example, the protective layer may be disposed at one or both outer sides in a stacking direction of a stack of the piezoelectric layer and the electrode layers. In addition, when a plurality of units in which the piezoelectric layer is installed between a pair of electrode layers is stacked, the protective layer may be disposed between the electrode layers adjacent in the stacking direction.

For example, when a force is applied in the stacking direction of the stack of the piezoelectric layer and the electrode layers (when the piezoelectric sensor is compressed), the protective layer elongates in the plane direction, and thereby a shear force acts on the piezoelectric layer and the electrode layers. Consequently, a tensile force in the plane direction is applied to the piezoelectric layer in addition to a pressing force in the stacking direction, and the strain of the piezoelectric layer increases. As a result, a quantity of electric charges generated in the piezoelectric layer increases, and the sensitivity of the sensor improves. The lower the Young's modulus of the protective layer, the more remarkable a sensitivity improving effect obtained by the protective layer. On the other hand, when a large shear force acts on the piezoelectric layer and the electrode layers, there is a concern that durability of both layers decreases. Therefore, from the viewpoint of durability, it is preferable that a product of the Young's modulus and a thickness of the protective layer is larger than a product of the Young's modulus and a thickness of the adjacent electrode layer, as described in the following Expression (III).

(Young's Modulus of Protective Layer×Thickness of Protective Layer)>(Young's Modulus of Electrode Layer×Thickness of Electrode Layer)    (III)

One or more elastomers selected from crosslinked rubbers and thermoplastic elastomers may also be used as the elastomer of the protective layer. Elastomers which are relatively low in Young's modulus and flexible and have a good adherence property to the electrode layer include natural rubber, isoprene rubber, butyl rubber, acrylic rubber, silicone rubber, urethane rubber, urea rubber, fluoro-rubber, NBR, and the like. In particular, when human biological information is measured, it is preferable to use silicone rubber or urethane rubber having an excellent affinity with a living body, and it is preferable that the elastomer do not contain a substance such as the plasticizer which dissolves out with time.

In order to decrease a change in sensitivity of the sensor when the sensor is repeatedly used, the protective layer preferably has excellent slumping resistance. In addition, the protective layer preferably has good wear durability and good tear durability to play a role of protecting the piezoelectric sensor from external mechanical stress.

A Poisson's ratio of the elastomer is about 0.5. Therefore, in the protective layer made of elastomer, a force applied in the thickness direction directly acts as a force in the plane direction. Therefore, the larger the thickness of the protective layer, the more a strain increasing effect of the piezoelectric layer increases, and the more the sensitivity improving effect of the sensor increases.

On the other hand, when the thickness of the protective layer increases, the thickness of the piezoelectric sensor increases, and the discomfort felt by the subject increases when the piezoelectric sensor is used as a biological information sensor. Therefore, a thickness of each one of the protective layers may be, for example, 5 μm or larger and 1,000 μm or smaller. In this specification, the thickness of the protective layer is a thickness of a region of one layer of the protective layers, the region being stacked on the electrode layer, as shown by a reference sign T in FIG. 3 described above.

<Piezoelectric Sensor>

The piezoelectric sensor has an elongated-sheet shape. A size of the piezoelectric sensor is not particularly limited as long as the piezoelectric sensor has an elongated size, that is, a length of 500 mm or longer. It is sufficient that at least the pressure sensing region in which the electrode layers overlap each other via the piezoelectric layer has a length of 500 mm or longer in a longitudinal direction thereof. When the pressure sensing region has a small width, the sensitivity decreases and it is difficult to detect weak vibration. The width of the pressure sensing region is preferably 10 mm or larger and more preferably 40 mm or larger. Conversely, when the pressure sensing region has a large width, the sensitivity increases; however, when the piezoelectric sensor is used as the biological information sensor, there is a concern that the discomfort felt by the subject increases, or air permeability is degraded and the subject is likely to sweat. The preferable width is 200 mm or smaller. The longer the length of the pressure sensing region, that is, the higher a rate of the length to the width, the more easily the subject's body overlaps the pressure sensing region, and thus the more easily the weak vibration due to respiration and heartbeats is detected. The preferable length is 550 mm or larger. On the other hand, from the viewpoint of easy installation on the bedding, the preferable length is 1,000 mm or shorter. When the pressure sensing region has a large thickness, the discomfort felt by the subject increases. The thickness is preferably 5 mm or smaller and even 2 mm or smaller.

The sensitivity of the piezoelectric sensor of the present disclosure is preferably 50 pC/N or higher. When the sensitivity is 50 pC/N or higher, the piezoelectric sensor is suitable as a biological information sensor that detects the weak vibration of the respiration or the heartbeats. In this specification, the sensitivity of the sensor is a value obtained by dividing a quantity of electric charges ($C/m^2$) generated per unit area by a load ($N/m^2$) applied per unit area.

<Method for Manufacturing Piezoelectric Sensor>

A manufacturing method of the present disclosure, which is one preferable method for manufacturing the piezoelectric sensor of the present disclosure, includes a coating-film forming step and a press-attaching step. Hereinafter, the steps will be described.

(1) Coating-Film Forming Step

This step is a step in which a conductive coating material for forming the electrode layers is coated on a surface of a base member by a die-coating method or a dispenser method to form an electrode-layer forming coating film.

The conductive coating material may be prepared by dispersing and dissolving a material (polymer of elastomer, flaky conductive materials, or the like) for forming the electrode layer in a solvent. The elastomer and the flaky conductive material are as described above. It is preferable that the solvent can dissolve the polymer of elastomer. For example, it is preferable to use butyl cellosolve acetate, acetylacetone or the like as the solvent. The conductive coating material may contain additives such as a cross-linker, a cross-linking promoter, a cross-linking aid, a dispersant, a plasticizer, a processing aid, an antioxidant, a softener, a colorant, an antifoaming agent, a leveling agent, a viscosity modifier and the like. The cross-linker, the cross-linking promoter, and the cross-linking aid which contribute to a cross-linking reaction may be appropriately selected depending on the kind of the elastomer. The plasticizer and the dispersant are as described above. When the flaky conductive materials contained in the electrode layer are flaky carbon materials, the conductive coating material may be prepared by the following two methods.

(i) First Preparation Method

The first preparation method includes a step of preparing a liquid composition containing an elastomer polymer, at least one of graphite powder and expanded graphite powder, and a solvent and a step of crushing the liquid composition using a wet jet mill.

Powder of natural graphite or artificial graphite may be used as the graphite powder. Powder of flake-formed graphite subjected to a flake forming process may be used. The expanded graphite is obtained by inserting a substance between layers of scale-like graphite, the substance generating gas when being heated. The expanded graphite powder may be the natural graphite or the artificial graphite. Powder of flake-formed expanded graphite subjected to the flake forming process may be used as the expanded graphite powder.

According to the wet jet mill, the liquid composition is pressurized by a high-pressure pump, sent into a nozzle and ejected from the nozzle at a high speed. Then, the graphite powder and the like in the liquid composition are crushed by a high shear force which is generated when the liquid composition passes through the nozzle, cavitation, and an impact force caused by impact with a wall or impact between the liquid compositions. According to the wet jet mill, peeling is easily proceed because the shear force is applied to the graphite powder or the expanded graphite powder. Consequently, it is possible to easily obtain nanometer-order multilayer graphene (flaky carbon materials). Processing pressure, a type of the nozzle, a nozzle diameter, the number of times of processing, and the like of the wet jet mill may be appropriately adjusted so that a desired flaky carbon material is obtained. From the viewpoint of proceeding the flake formation, a nozzle having a shape that easily causes the impact with the wall or the impact between the liquid compositions, for example, an impact (cross) nozzle or the like, may be selected as the type of the nozzle. Besides, it is preferable to repeat the crushing two or more times. In other words, it is preferable to eject the liquid composition from the nozzle of the wet jet mill two or more times.

(ii) Second Preparation Method

The second preparation method includes a step in which graphite-powder dispersion liquid containing at least one of the graphite powder and the expanded graphite powder and a solvent is crushed using the wet jet mill and a step in which an elastomer solution containing the elastomer polymer and a solvent is added to the graphite-powder dispersion liquid subjected to the crushing to prepare the liquid composition.

The second preparation method is different from the first preparation method in that the graphite-powder dispersion liquid instead of the liquid composition is subjected to the crushing. The crushing performed by the wet jet mill is the same as that in the first preparation method. It is preferable that the solvent of the graphite-powder dispersion liquid is the same as the solvent of the elastomer solution. In addition, when a dispersant is used in the second preparation method, it is preferable that the dispersant is blended with the graphite-powder dispersion liquid.

The base member that is coated with the conductive coating material is not particularly limited as long as the electrode-layer forming coating film can be formed by the die-coating method or the dispenser method. For example, the base member includes a resin film consisting of polyethylene terephthalate (PET), polyethylene naphthalate (PEN), polyimide, polyethylene and the like. The base member is preferably a base member subjected to a release treatment so that the formed electrode-layer forming coating film easily peels off.

The coating of the conductive coating material is performed by the die-coating method or the dispenser method. The flaky conductive materials are dispersed in the liquid conductive coating material in random directions. When the die-coating method and the dispenser method are used, a shear force in one direction is applied to the conductive coating material. The flaky conductive materials contained in the conductive coating material are oriented by the shear force in a manner that the length direction thereof is coincident with the forming direction of the coating film, that is, the length direction of the flaky conductive materials is horizontal with respect to the surface of the coating film. Consequently, a conduction path is easily formed in the longitudinal direction of the electrode layer. As a result, the electrical resistance is unlikely to increase even when the length of the electrode layers increases, and high conductivity can be realized. In addition, when the flaky conductive materials are oriented, unevenness of the surface of the coating film decreases, an adhering area with the piezoelectric layer increases and adhesiveness can be increased. When the unevenness of the surface of the electrode layer decreases, a gap between the piezoelectric layer and the electrode layer decreases, and thus the sensitivity of the piezoelectric sensor is effectively improved. Among the die-coating methods, a lip die-coating method is preferably used from a reason that it is possible to apply a large shear force to the conductive coating material.

In this step, after the conductive coating material is coated, the coating film may be heated or the like at a predetermined temperature to be appropriately dried. However, the coating film should be used in the next press-attaching step in a state that cross-linking of the coating film is not completed. In other words, the electrode-layer forming coating film formed in this step is in a non-cross-linked or cross-linking proceeding state (hereinafter, appropriately referred to as a "half-cross-linked state").

As described above, when the surface, which is among the surfaces of the electrode-layer forming coating film and is press-attached to the piezoelectric layer, has low unevenness, the adhering area with the piezoelectric layer increases, and the adhesiveness increases. Accordingly, surface roughness (arithmetic average roughness: Ra) of the electrode-layer forming coating film formed in this step is preferably 6 μm or lower.

(2) Press-Attaching Step

This step is a step in which the electrode-layer forming coating film and the piezoelectric layer are overlapped and press-attached before cross-linking of the electrode-layer forming coating film formed in the previous step is completed.

In this step, the half-cross-linked electrode-layer forming coating film formed in the previous step and the piezoelectric layer are press-attached. The surface of the electrode-layer forming coating film is further smoothened by the press-attaching. Consequently, the adhering area with the piezoelectric layer further increases, and the adhesiveness can be further increased. When the adhesiveness is high, in addition to improvement in sensitivity of the piezoelectric sensor, the piezoelectric layer and the electrode layers are unlikely to peel off even when extending and contracting are repeated, and thus durability of the sensor improves. Preferably, any one or more of a press machine, a vacuum press machine, a roll press machine, and a thermocompression laminator is used in the press-attaching. For example, preferably, the press-attaching is performed in a condition of a temperature of 50° C. or higher and 140° C. or lower and a pressure of 50 kPa or higher and 300 kPa or lower. In addition, as described above, from the viewpoint of increasing adhesiveness between the piezoelectric layer and the electrode layer, the peeling strength of the electrode layer with respect to the piezoelectric layer is preferably 2 N/25 mm or higher. The cross-linking of the electrode-layer forming coating film is completed by the press-attaching, and the electrode layer is formed.

EXAMPLES

Next, examples are provided to specifically describe the present disclosure.

(1) Relationship between Electrode Layer and Sensor Sensitivity Six types of piezoelectric sensors were manufactured by modifying the electrode layers, and sensor sensitivity of the sensors was measured.

<Manufacturing of Piezoelectric Layer>

First, 100 parts by mass of carboxyl group-modified hydrogenated nitrile rubber ("Therban (registered trademark) XT8889" manufactured by Lanxess) serving as the elastomer were dissolved in acetylacetone to prepare a polymer solution. Next, 350 parts by mass of single-particle powder of lithium sodium potassium niobate serving as the piezoelectric particles were added and kneaded in the prepared polymer solution. Subsequently, the kneaded product repeatedly passed through three rolls for five times, and slurry was obtained. Then, 5 parts by mass of tetrakis(2-ethylhexyloxy)titanium of the cross-linker were added to the obtained slurry and kneaded by an air agitator, and then the slurry is coated on the base member by the die-coating method. A PET film subjected to the release treatment was used as the base member. A die coater (manufactured by Techno Machine Co., Ltd) was used in the coating of the slurry. The coating film was heated at 150° C. for one hour, and a piezoelectric layer having a thickness of 35 jam was manufactured. The content of the piezoelectric particles in the piezoelectric layer is 48 volume % when the elastomer is set as 100 volume %.

The single-particle powder of lithium sodium potassium niobate that was used was manufactured as follows.

(1) First Mixing Step

As a raw material, powders of $K_2CO_3$, $Na_2CO_3$, $Nb_2O_5$, and $Li_2CO_3$ were used. The powders were weighed based on a composition of a target sintered body $(Li_{0.06}L_{0.047}Na_{0.47}Nb_{1.0})O_3$ and, then, were wet-mixed in anhydrous acetone for 16 hours. The obtained mixed powder was subjected to evaporation and was further dried in an oven, and acetone is volatilized.

(2) Temporary Firing Step

The mixed powder obtained after the volatilization of acetone was put into an alumina crucible, and the crucible was put in one big crucible. The inner crucible was disposed in a face-down state so as to cover the mixed powder. The double crucibles are put in an electric furnace, and temporary firing was performed at 910° C. for ten hours.

(3) Second Mixing Step

The obtained temporarily-fired product was crushed into powder in a mortar. The powder was mixed in anhydrous acetone for 16 hours. The obtained mixed powder was subjected to evaporation and was further dried in an oven, and acetone is volatilized.

(4) Final Firing Step

Similarly to (2), the mixed powder after the volatilization of acetone was put in double crucibles and was fired at 150° C. for one hour, at 550° C. for three hours, and at 1,082° C. for a half hour.

(5) Crushing Step

The obtained fired product was crushed into single particles in a ball mill, and single-particle powder of lithium sodium potassium niobate was obtained.

<Manufacturing of Electrode Layer>

[Electrode Layer 1]

First, 35 parts by mass of flake-formed graphite powder, 25 parts by mass of dispersant, 6 parts by mass of cross-linker, and 1 part by mass of cross-linking promoter were added to the polymer solution obtained by dissolving 68 parts by mass of glycidyl ether group-modified acrylic rubber polymer serving as the elastomer in butyl cellosolve acetate, and the conductive coating material was prepared (the materials are described later in detail). Next, the prepared conductive coating material was crushed by the wet jet mill ("Nanovater (registered trademark)" manufactured by Yoshida Machine Kogyo Co., Ltd). The crushing was performed six times in total by pass driving (six-pass process). In the first pass, the crushing was performed in a straight nozzle (having a nozzle diameter of 170 μm) with a processing pressure of 90 MPa, and in the second and the following passes, the crushing was performed in a cross nozzle (having a nozzle diameter of 170 μm) with a processing pressure of 130 MP. The conductive coating material obtained after the crushing is coated on the base member by the die-coating method. The PET film subjected to the release treatment was used as the base member. The die coater (same as above) was used in the coating of the conductive coating material. The coating film was heated at 150° C. for ten minutes, and an electrode layer 1 having a thickness of 20 μm was manufactured. At this time, that is, before the coating film is press-attached to the piezoelectric layer, the cross-linking of the electrode layer 1 is not completed (the same applies to electrode layers 2 to 5 below using an elastomer polymer). Hereinafter, the electrode layer 1 at this time is referred to as the "half-cross-linked" electrode layer 1 in some cases.

The glycidyl ether group-modified acrylic rubber polymer was manufactured by suspension polymerization of three kinds of monomers. Ethyl acrylate (EA), acrylonitrile (AN), and allyl glycidyl ether (AGE) were used as the monomers. As for a blending ratio of the monomers, the ratio of EA is set to 96 mass %, the ratio of AN is set to 2 mass %, and the ratio of AGE is set to 2 mass %. The Tg of the obtained acrylic rubber polymer was −10° C.

As the flake-formed graphite powder, "iGurafen-α" (having an average particle size of 87.2 μm) manufactured by Itec Co., Ltd was used. As the dispersant, the high-molecular-weight polyester acid amidoamine salt ("Disparlon (registered trademark) DA7301" manufactured by Kusumoto Chemicals, Ltd) was used. As the cross-linker, amino-terminated butadiene-acrylonitrile copolymer ("ATBN1300×16" manufactured by CVC Thermoset Specialties Ltd.) was used. As the cross-linking promoter, a zinc complex ("XK-614" manufactured by KING INDUSTRIES, INC) was used.

[Electrode Layer 2]

First, as the flaky conductive materials, 300 parts by mass of primary silver particles ("Nanomelt Ag-XF301S" manufactured by FUKUDA METAL FOIL & POWDER CO., LTD) and 50 parts by mass of secondary silver particles ("FA-STG-111" manufactured by DOWA Electronics Materials Co., Ltd) were added to a polymer solution obtained by dissolving 100 parts by mass of epoxy group-containing acrylic rubber polymer-A ("Nipol (registered trademark) AR51" manufactured by Nippon Zeon Co., Ltd, Tg: −14° C.) serving as the elastomer in butyl cellosolve acetate, and the obtained product is dispersed by three rolls to prepare a conductive coating material. Subsequently, the conductive coating material is coated on the base member by the die-coating method. The PET film subjected to the release treatment was used as the base member. The die coater (same as above) was used in the coating of the conductive coating material. The coating film was heated at 150° C. for ten minutes, and the electrode layer 2 having a thickness of 20 μm was manufactured.

[Electrode Layer 3]

The electrode layer 3 was manufactured similarly to the electrode layer 1 except that, in the manufacturing of the electrode layer 1, a blending amount of the flake-formed graphite powder is increased to 50 parts by mass, and the zinc complex of the cross-linking promoter was not blended.

[Electrode Layer 4]

First, 10 parts by mass of conductive carbon black ("Ketjenblack EC600JD" manufactured by Lion Corporation), 16 parts by mass of carbon nanotubes ("VGCF (registered trademark)" manufactured by Showa Denko K.K.), and 12 parts by mass of high-molecular-weight polyester acid amidoamine salt (same as above) serving as the dispersant were added to a polymer solution obtained by dissolving 100 parts by mass of epoxy group-containing acrylic rubber polymer-B ("Nipol (registered trademark) AR42 W" manufactured by Nippon Zeon Co., Ltd, Tg: −26° C.) serving as the elastomer in butyl cellosolve acetate, and the obtained product is dispersed by a bead mill to prepare a conductive coating material. Subsequently, the conductive coating material is coated on the base member by the die-coating method. The PET film subjected to the release treatment was used as the base member. The die coater (same as above) was used in the coating of the conductive coating material. The coating film was heated at 150° C. for ten minutes, and the electrode layer 4 having a thickness of 20 μm was manufactured.

[Electrode Layer 5]

The electrode layer 5 was manufactured similarly to the electrode layer 4 except that, in the manufacturing of the electrode layer 4, the conductive coating material was prepared without blending carbon nanotubes and the dispersant.

[Electrode Layer 6]

Silver paste ("Dotite (registered trademark) D-362" manufactured by Fujikura Kasei Co., Ltd) is coated on the base member. The PET film subjected to the release treatment was used as the base member. The die coater (same as above) was used in the coating of the conductive coating material. The coating film was heated at 150° C. for one hour, and the electrode layer 6 having a thickness of 20 μm was manufactured.

<Manufacturing of Protective Layer>

A thermoplastic elastomer film ("ESMER (registered trademark) URS-ET" manufactured by Nihon Matai Co., Ltd and having a thickness of 250 μm) was cut into a predetermined size, and the protective layer was obtained.

<Manufacturing of Piezoelectric Sensor>

The electrode layers 1 to 6 were combined with the piezoelectric layer and the protective layer, and six types of piezoelectric sensors were manufactured as described below. One piezoelectric sensor has two electrode layers (first electrode layer and second electrode layer), and the two electrode layers are the same as each other. The piezoelectric layer and the electrode layers 1 to 6 are peeled from the base member after overlapping counterpart members.

First, a hot-melt film ("ELFAN (registered trademark) UH-203" manufactured by Nihon Matai Co., Ltd) serving as an adhesive was attached to the thermoplastic elastomer film of the protective layer. In the attachment of the film, laminator-A ("LPD3223" manufactured by FUJIPLA Co., Ltd.) was used. Next, the half-cross-linked electrode layer overlapped the hot-melt film of the protective layer, and the layer and the film were press-attached using a vacuum press machine. The press-attaching was performed in a condition of a temperature of 80° C., a load of 300 kPa, and a time of 60 seconds. Subsequently, the piezoelectric layer overlapped the press-attached electrode layer, and the layers were press-attached using the vacuum press machine in the same press-attaching condition. Then, the half-cross-linked electrode layer overlapped the press-attached piezoelectric layer, and the layers were press-attached using the vacuum press machine in the same press-attaching condition. Finally, the hot-melt film of the protective layer overlapped the press-attached electrode layer, and the film and the layer were press-attached using the vacuum press machine in the same press-attaching condition.

As described above, a stack of the protective layer/the electrode layer/the piezoelectric layer/the electrode layer/the protective layer was obtained (for convenience of description, an adhesive layer between the protective layer and the electrode layer is omitted). A DC power supply was connected to the two electrode layers of the obtained stack, the polarization treatment was performed by applying an electric field of 20 V/μm to the piezoelectric layer for ten minutes, and the piezoelectric sensor having an elongated-sheet shape was manufactured. The pressure sensing region in the piezoelectric sensor has a rectangular shape having a width of 40 mm and a length of 900 mm.

<Measurement of Young's Modulus>

The Young's moduli of the piezoelectric layer, the electrode layer, and the protective layer were calculated from a stress-elongation curve obtained by performing a tensile test which is prescribed in JIS K 7127: 1999. The tensile test was performed by using the test piece type 2 at a tensile speed of 100 mm/min. From the tensile test, the electrode layers 1 to 5 were verified to be capable of elongating by 10% or more in the longitudinal direction. The electrode layer 6 was not capable of elongating up to 10%.

<Measurement of Electrical Resistance of Electrode Layer>

The electrical resistance between two points in the longitudinal direction in the pressure sensing region (rectangular shape having a width of 40 mm and a length of 900 mm)

of the electrode layer was measured. Specifically, a left end portion (point A in FIG. 2 described above and one end portion in the present disclosure) was set as a base point (0 mm), points separated from the base point by 100 mm, 300 mm, 600 mm, and 900 mm on a straight line in the longitudinal direction were set as measurement points, and the electrical resistances between the base point and the measurement points were measured by a tester. Moreover, the point separated from the base point by 900 mm on a straight line is a right end portion (point B in the same figure and the other end portion in the present disclosure) of the pressure sensing region.

<Measurement of Sensor Sensitivity>

The manufactured piezoelectric sensor was installed in a fatigue durability tester ("MMT-101N" manufactured by Shimadzu Corporation), and sin waves (frequency of 1 Hz) of loads 2.5N±1.5N, 4.5N±3.5N, and 6.5N±5.5N in a compression direction were applied in this order to measurement locations described later by a compression jig (20 mm×30 mm). In this case, an amount of generated electric charges was measured using a charge amplifier ("NEXUS Charge Amplifier type2692" manufactured by Briiel & Kjer) and an oscilloscope ("DLM2022" manufactured by Yokogawa Electric Corporation). Then, an average value was calculated by dividing the amount of generated electric charges (unit: Coulomb) measured for each of the loads by an applied compressive force (unit: Newton) and was set as the sensor sensitivity (Coulomb/Newton: C/N) at the measurement locations of the piezoelectric sensor. The measurement locations were set as four points separated from the base point (point A in FIG. 2 described above) set when the electrical resistance was measured, the four points being separated from the base point by 100 mm, 300 mm, 600 mm, and 700 mm on a straight line in the longitudinal direction.

<Measurement of Sensor Sensitivity During Elongation by 10%>

The sensor sensitivity at the point separated from the base point by 100 mm on a straight line in the longitudinal direction was measured in the same manner as described above except that the fatigue durability tester (same as above) was installed in a state that the piezoelectric sensor is elongated by 10% in the longitudinal direction.

<Measurement Result>

Table 1 shows a configuration and sensitivity of the manufactured piezoelectric sensor, the electrical resistance of the electrode layer, and the like. In this example, the two electrode layers disposed at both sides of the piezoelectric layer are the same as each other. Thus, whether or not the above Expression (I) is satisfied is determined depending on whether or not a value of $[(Y_p \times T_p)/(Y_e \times T_e \times 2)]$ corresponding to a left side in the above Expression (Ib) is 1 or larger.

TABLE 1

| Piezoelectric sensor | | | Example 1 | Example 2 | Comparative Example 1 | Comparative Example 2 | Comparative Example 3 | Comparative Example 4 |
|---|---|---|---|---|---|---|---|---|
| Configuration | Piezoelectric layer | Young's modulus (Yp) [MPa] | 80 | | | | | |
| | | Thickness (Tp) [mm] | 0.035 | | | | | |
| | | | Electrode layer 1 | Electrode layer 2 | Electrode layer 3 | Electrode layer 4 | Electrode layer 5 | Electrode layer 6 |
| | Electrode layer | Young's modulus (Ye) [MPa] | 35 | 20 | 75 | 25 | 2 | 450 |
| | | Thickness (Te) [mm] | 0.02 | | | | | |
| | | Electrical resistance in zone of 100 mm [Ω] | 38 | 1 | 34 | 317 | 4917 | 1> |
| | | Electrical resistance in zone of 300 mm [Ω] | 225 | 3 | 205 | 1,900 | 29,500 | 1> |
| | | Electrical resistance in zone of 600 mm [Ω] | 450 | 6 | 410 | 3,800 | 59,000 | 1> |
| | | Electrical resistance in zone of 900 mm [Ω] | 675 | 9 | 615 | 5,700 | 88,500 | 1> |
| | Protective layer | Young's modulus (Yc) [MPa] | 20 | | | | | |
| | | Thickness (Tc) [mm] | 0.25 | | | | | |
| Properties | Sensor sensitivity at point from one end portion by 100 mm [pC/N] | | 72 | 88 | 44 | 75 | 110 | 25 |
| | Sensor sensitivity at point from one end portion by 300 mm [pC/N] | | 72 | 88 | 44 | 75 | 10 | 25 |
| | Sensor sensitivity at point from one end portion by 600 mm [pC/N] | | 73 | 89 | 44 | 45 | 5 | 25 |

TABLE 1-continued

| | | | | | | |
|---|---|---|---|---|---|---|
| Sensor sensitivity at point from one end portion by 700 mm [pC/N] | 72 | 87 | 44 | 18 | 1 or lower | 25 |
| (Yp × Tp)/(Ye × Te × 2) | 2.0 | 3.5 | 0.9 | 2.8 | 35.0 | 0.2 |
| Determination on whether or not Expression (I) is satisfied | ○ | ○ | x | ○ | ○ | x |
| Sensor sensitivity during elongation of 10% (point of 100 mm) [pC/N] | 77 | 83 | 49 | 75 | 115 | Indeterminable |

As shown in Table 1, the following was verified. In the electrode layers 1 and 2 containing the flaky conductive material, the electrical resistance of the space (the measurement zone) between both end portions by which a distance between the two points was the longest was 3,000Ω or lower, the Young's modulus was low, and the piezoelectric sensors of Examples 1 and 2 using the electrode layers satisfied the above Expression (I). Besides, in the piezoelectric sensors of Examples 1 and 2, the sensitivity was increased to 50 pC/N or higher at any measurement points, and the high sensitivity was maintained even when the elongation of 10% was performed. Moreover, when the electrode layer 1 is compared with the electrode layer 2, the electrode layer 2 has a lower electrical resistance and a higher sensor sensitivity. However, the electrode layer 2 is formed using the silver particles as the flaky conductive materials, and thus the cost thereof increases. Therefore, in application in which the electrode layer has a large area or the like, it is preferable to use the electrode layer 1 formed using the carbon materials as the flaky conductive materials.

In contrast, the electrode layer 3 contains many flaky conductive materials. Thus, in the electrode layer 3, the electrical resistance was low, but the Young's modulus was higher than the electrical resistance of the electrode layer 1. Therefore, a piezoelectric sensor of Comparative Example 1 did not satisfy the above Expression (I). In addition, in the piezoelectric sensor of Comparative Example 1, the electrode layer 3 was inflexible, and thus sensitivity decreased. The electrode layers 4 and 5 do not contain the flaky conductive materials. Thus, in the electrode layers 4 and 5, the electrical resistance significantly increased as the distance increased between the two points at which the electrical resistance was measured. Accordingly, in piezoelectric sensors of Comparative Examples 2 and 3 using the electrode layers 4 and 5, the sensitivity decreased as the measurement point is separated from the base point. The electrode layer 6 is made of silver paste. In the electrode layer 6, the electrical resistance is low, but the Young's modulus increases, and the electrode layer is inflexible. Therefore, the electrode layer 6 was not capable of elongating up to 10%. In addition, a piezoelectric sensor of Comparative Example 4 using the electrode layer 6 did not satisfy the above Expression (I), and the sensitivity also decreased.

(2) Influence of Difference in Manufacturing Method on Sensor Sensitivity

With the same configuration and size as that of the piezoelectric sensor of Example 1 having the electrode layer 1, at least one of the method for forming the electrode layer 1, a cross-linking state of the electrode layer 1 before the press-attaching, and a press-attaching method when the stack is manufactured is changed to further manufacture seven types of piezoelectric sensors, and the sensor sensitivity of each piezoelectric sensor was measured.

Manufacturing of Piezoelectric Sensor

Reference Example 1

The method for forming the electrode layer 1 was changed to the lip die-coating method, and the coating of the conductive coating material was performed using a lip die coater ("test coater" manufactured by Oriental Packaging Materials Co., Ltd). A piezoelectric sensor having the electrode layer manufactured in this way was set as Reference Example 1.

Reference Example 2

The method for forming the electrode layer 1 was changed to the dispenser method, and the coating of the conductive coating material was performed using a dispenser ("air-pulse dispenser" manufactured by Musashi Engineering Inc). In the dispenser, a flat nozzle having a slit of 3.0 mm was used. A piezoelectric sensor having the electrode layer manufactured in this way was set as Reference Example 2.

Reference Example 3

The method for forming the electrode layer 1 is changed to a screen-printing method, and the conductive coating material is screen-printed on the base member. A piezoelectric sensor having the electrode layer manufactured in this way was set as Reference Example 3.

Reference Example 4

Both the method for forming the electrode layer 1 and the press-attaching method when the stack is manufactured are changed. The lip die-coating method was employed, and the coating of the conductive coating material was performed using the lip die coater (same as above). Then, the press-attachment of the layers was performed as follows. First, the half-cross-linked electrode layer overlapped the hot-melt film of the protective layer, and both the film and the layer passed between the rolls of a laminator-B (thermocompression laminator manufactured by MCK) so as to be press-attached to each other. The press-attaching was performed in a condition of a temperature of 125° C., a pressure of 196 kPa, and a movement speed of 0.5 m/min. Next, the piezoelectric layer overlapped the press-attached electrode layer, and the layers were press-attached using the same device in the same press-attaching condition. Subsequently, the half-cross-linked electrode layer overlapped the press-attached piezoelectric layer, and the layers were press-attached using the same device in the same press-attaching condition. Finally, the hot-melt film of the protective layer overlapped the press-attached electrode layer, and the film and the layer were press-attached using the same device in the same press-attaching condition. A piezoelectric sensor having the electrode layer manufactured in this way was set as Reference Example 4.

Reference Example 5

Both the method for forming the electrode layer 1 and the press-attaching method when the stack is manufactured are changed. The lip die-coating method was employed, and the coating of the conductive coating material was performed using the lip die coater (same as above). Then, the press-attachment of the layers was performed as follows. First, the half-cross-linked electrode layer overlapped the hot-melt film of the protective layer, and the layer and the film were press-attached using the laminator-A (same as above). The press-attaching was performed in a condition of a temperature of 117° C. and a pressure of 20 kPa. Next, the piezoelectric layer overlapped the press-attached electrode layer, and the layers were press-attached using the same device in the same press-attaching condition. Subsequently, the half-cross-linked electrode layer overlapped the press-attached piezoelectric layer, and the layers were press-attached using the same device in the same press-attaching condition. Finally, the hot-melt film of the protective layer overlapped the press-attached electrode layer, and the film and the layer were press-attached using the same device in the same press-attaching condition. A piezoelectric sensor having the electrode layer manufactured in this way was set as Reference Example 5.

Reference Example 6

Only the cross-linking state of the electrode layer 1 before the press-attaching was changed. In other words, after the coating of the conductive coating material was performed using the die coater, the coating film was heated at 150° C. for one hour, the cross-linking was completed, and then the stack was manufactured. A piezoelectric sensor having the electrode layer manufactured in this way was set as Reference Example 6.

Reference Example 7

Both the method for forming the electrode layer 1 and the cross-linking state before the press-attaching changed. The coating of the conductive coating material was performed by screen printing. Then, the coating film was heated at 150° C. for one hour, the cross-linking was completed, and then the stack was manufactured. A piezoelectric sensor having the electrode layer manufactured in this way was set as Reference Example 7.

<Measurement of Surface Roughness of Electrode Layer>

As for the coating film of the electrode layer before the stack was manufactured, the arithmetic average roughness (Ra) of the surface attached to the piezoelectric layer was measured by a shape measuring laser microscope (laser microscope) "VK-X100" manufactured by Keyence corporation. A viewing angle during the measurement was in a square of 10 mm, and the surface roughness of the entire square of 10 mm was measured.

<Measurement of Peeling Strength>

A sample in which the piezoelectric layer and the electrode layers were press-attached in a press-attachment width of 25 mm was prepared in respective press-attachment conditions when the piezoelectric sensors of Example 1 and Reference Examples 1 to 7 were manufactured. In the samples that are manufactured, the 90° peeling test in accordance with JIS Z 0237: 2009 was performed (peeling width of 25 mm, peeling length of 100 mm, and tensile speed of 300 mm/min), and the peeling strength was measured. Moreover, in the peeling test, when at least one of the piezoelectric layer and the electrode layer is broken, the test result was determined as "material breakage".

<Measurement Result>

Table 2 collectively shows the coating-film forming step and the press-attaching step in the method for manufacturing the piezoelectric sensor, the surface roughness of the electrode layer, the peeling strength, and the sensitivity of the piezoelectric sensor.

TABLE 2

| | | Example 1 | Reference Example 1 | Reference Example 2 | Reference Example 3 | Reference Example 4 | Reference Example 5 | Reference Example 6 | Reference Example 7 |
|---|---|---|---|---|---|---|---|---|---|
| Electrode layer 1 | Coating-film forming step | Die coating | Lip die-coating | Dispenser | Screen printing | Lip die-coating | Lip die-coating | Die coating | Screen printing |
| | Press-attaching step — Cross-linked state of coating film | Half-cross-linked | Half-cross-linked | Half-cross-linked | Half-cross-linked | Half-cross-linked | Half-cross-linked | Cross-linked | Cross-linked |
| | Press-attaching method | Vacuum press | Vacuum press | Vacuum press | Vacuum press | Laminator B | Laminator A | Vacuum press | Vacuum press |
| | Surface roughness (Ra) [µm] | 4.0 | 3.5 | 4.5 | 8.5 | 3.5 | 3.5 | 4.0 | 8.5 |
| | Peeling strength [N/25mm] | Material breakage | Material breakage | Material breakage | 1 or lower | Material breakage | 1 or lower | 1 or lower | 1 or lower |
| Properties of piezoelectric sensor | Sensor sensitivity at point from one end portion by 100 mm [pC/N] | 72 | 72 | 71 | 68 | 72 | 69 | 67 | 48 |
| | Sensor sensitivity at point from one end portion by 300 mm [pC/N] | 72 | 72 | 71 | 68 | 72 | 69 | 67 | 48 |
| | Sensor sensitivity at point from one end portion by 600 mm [pC/N] | 73 | 73 | 71 | 68 | 73 | 69 | 66 | 48 |
| | Sensor sensitivity at point from one end portion by 700 mm [pC/N] | 72 | 72 | 72 | 68 | 72 | 68 | 66 | 48 |

As shown in Table 2, when the electrode-layer forming coating film was formed using the die-coating method, the lip die-coating method, or the dispenser method, the shear force was applied to the conductive coating material during the coating, and thereby a plane of the flaky carbon materials that are contained was easily oriented along the plane direction of the coating film, and the surface roughness (Ra) of the coating film decreased to 6 μm or lower. In contrast, when the coating was performed by the screen-printing method, the shear force is not applied to the conductive coating material during the coating, orientation depends on leveling properties of the conductive coating material, and thus it is difficult for the flaky carbon materials to be oriented. Therefore, the surface roughness of the coating film increased. As described in Reference Examples 3 and 7, when the surface roughness is high, the peeling strength decreases, leading to a decrease in durability. In addition, a decrease in contact area with the piezoelectric layer results in a decrease in adhesiveness to the piezoelectric layer and a decrease in sensor sensitivity.

When the stack (piezoelectric sensor) is manufactured after the cross-linking of the electrode-layer forming coating film is completed, an adhering effect due to pressurizing decreases. Hence, as shown in Reference Examples 6 and 7, the peeling strength decreases, leading to a decrease in durability. In addition, the adhesiveness to the piezoelectric layer decreases, leading to a decrease in sensor sensitivity. In addition, as shown in Reference Examples 4 and 5, when the press-attaching conditions were different, a difference in adhering effect of the pressurization occurs, and thus a difference in peeling strength is verified.

INDUSTRIAL APPLICABILITY

The piezoelectric sensor of the present disclosure is used as a biological information sensor that measures a respiration state, a heart rate or the like in a medical field, a rehabilitation field, a nursing field, a healthcare field, a training field, a driver monitoring system which performs vital sensing of an automobile, or the like.

REFERENCE SIGNS LIST

1: biological information detecting device
10: piezoelectric sensor
11: piezoelectric layer
12a, 12b: electrode layer
13a, 13b: protective layer
20a, 20b: wiring
30: control circuit unit
40: cover
P: subject
S: pressure sensing region

What is claimed is:

1. A method for manufacturing piezoelectric sensor, which manufactures a piezoelectric sensor having an elongated-sheet shape and comprising:
    a piezoelectric layer containing a first elastomer and piezoelectric particles; and
    electrode layers which are disposed with the piezoelectric layer sandwiched between the electrode layers, and
    a protective layer, stacked on at least one of the electrode layers and contains a second elastomer,
    wherein a product of Young's modulus and a thickness of the protective layer is larger than a product of Young's modulus and a thickness of the electrode layers adjacent to the protective layer,
    wherein, when a region in which the electrode layers overlap each other via the piezoelectric layer is set as a pressure sensing region, the pressure sensing region has a length of 500 mm or longer in a longitudinal direction thereof,
    wherein the electrode layers contain a third elastomer and flaky conductive materials and are capable of elongating by 10% or more in one direction of plane directions, and when a space between one end portion and the other end portion of the pressure sensing region in the longitudinal direction is set as a measurement zone, an electrical resistance in the measurement zone in the electrode layers is 3,000Ω or lower,
    a length direction of the flaky conductive materials is horizontal with respect to surfaces of the electrode layers, and
    wherein, when the electrode layers disposed with one piezoelectric layer sandwiched therebetween are set as a first electrode layer and a second electrode layer, the following Expression (I) is satisfied:

(Young's Modulus of Piezoelectric Layer×Thickness of Piezoelectric Layer)≥{(Young's Modulus of First Electrode Layer×Thickness of First Electrode Layer)+(Young's Modulus of Second Electrode Layer×Thickness of Second Electrode Layer)}  (I), the method for manufacturing piezoelectric sensor comprises:
    a coating-film forming step in which a conductive coating material for forming the electrode layers is coated on a surface of a base member by a die-coating method or a dispenser method to form an electrode-layer forming coating film;
    a press-attaching step in which the electrode-layer forming coating film and the piezoelectric layer are overlapped and press-attached before cross-linking of the formed electrode-layer forming coating film is completed, and
    a cross-linking step.

2. The method for manufacturing piezoelectric sensor according to claim 1,
    wherein at least one of a press machine, a vacuum press machine, a roll press machine, and a thermocompression laminator is used in the press-attaching step.

3. The method for manufacturing piezoelectric sensor according to claim 1,
    wherein a surface of the electrode-layer forming coating film which is attached to the piezoelectric layer has an arithmetic average roughness (Ra) of 6 μm or lower.

4. The method for manufacturing piezoelectric sensor according to claim 1, wherein, in the coating-film forming step, the conductive coating material comprises flaky conductive materials, and the flaky conductive materials are dispersed in the liquid conductive coating material in random directions, and
    in the press-attaching step, a shear force in one direction is applied to the conductive coating material, the flaky conductive materials contained in the conductive coating material are oriented by the shear force in a manner that a length direction of the flaky conductive materials is horizontal with respect to a surface of the electrode-layer forming coating film.

* * * * *